United States Patent
Lee

(10) Patent No.: US 10,369,341 B2
(45) Date of Patent: Aug. 6, 2019

(54) MICRO NEEDLE DRIVING DEVICE

(71) Applicant: LAON CO., LTD., Siheung-si (KR)

(72) Inventor: Doo Won Lee, Ansan-si (KR)

(73) Assignee: LAON CO., LTD., Siheung-si (KR)

(*) Notice: Subject to any disclaimer, the term of this patent is extended or adjusted under 35 U.S.C. 154(b) by 246 days.

(21) Appl. No.: 15/302,017

(22) PCT Filed: Apr. 24, 2015

(86) PCT No.: PCT/KR2015/004124
§ 371 (c)(1),
(2) Date: Oct. 5, 2016

(87) PCT Pub. No.: WO2015/163731
PCT Pub. Date: Oct. 29, 2015

(65) Prior Publication Data
US 2017/0120024 A1    May 4, 2017

(30) Foreign Application Priority Data
Apr. 25, 2014 (KR) .......................... 10-2014-0049905

(51) Int. Cl.
A61M 37/00 (2006.01)
A61H 39/08 (2006.01)
A61M 5/158 (2006.01)
A61M 5/14 (2006.01)

(52) U.S. Cl.
CPC ......... A61M 37/0015 (2013.01); A61H 39/08 (2013.01); A61M 5/158 (2013.01); A61M 37/00 (2013.01); A61M 5/14 (2013.01); A61M 2037/0023 (2013.01)

(58) Field of Classification Search
CPC .................. A61M 37/0015; A61H 39/08
USPC .......................... 606/133, 185, 186
See application file for complete search history.

(56) References Cited

U.S. PATENT DOCUMENTS 6,689,072 B2 * 2/2004 Kaplan .......... A61B 10/0233
600/564

FOREIGN PATENT DOCUMENTS

| KR | 200428918 | 10/2006 |
| KR | 100922138 | 10/2009 |
| KR | 20100091617 | 8/2010 |
| KR | 20110040307 | 4/2011 |

(Continued)

OTHER PUBLICATIONS

International Search Report—PCT/KR2015/004124 dated Jun. 22, 2015.

Primary Examiner — Vy Q Bui
(74) Attorney, Agent, or Firm — Novick, Kim & Lee, PLLC; Jae Youn Kim

(57) ABSTRACT

A micro needle driving device comprises: a main body having a receiving space formed therein; a drive motor provided in the receiving space; a rotating unit axially coupled to and rotating with the rotating shaft of the drive motor and having a guide projection formed on an outer peripheral side surface thereof; and a moving cam unit having the micro needle unit coupled to a side thereof and the rotating unit received therein, having a guide portion formed in a curved line along a lengthwise direction on an inner peripheral side surface thereof, and reciprocally and linearly moved according to the rotation of the rotating unit. The guide portion has the guide projection connected thereto in a slidably movable manner.

4 Claims, 3 Drawing Sheets

(56) References Cited

FOREIGN PATENT DOCUMENTS

KR          20130116095          10/2013

\* cited by examiner

MICRO NEEDLE DRIVING DEVICE

TECHNICAL FIELD

The present invention relates to a micro needle driving device, and more particularly to a micro needle driving device that has a simple structure, thereby allowing an economical and precise control thereof and improving durability.

BACKGROUND ART

In general, in order to prevent wrinkles or treat skin troubles, cosmetics or treating agents containing a specific substance are applied or sprayed on skin. However, because the supplied substance cannot easily pass through the stratum corneum of the skin, the method is not effective. Accordingly, in order to solve the disadvantage, an apparatus of a so-called "a micro needle" has been developed.

The micro needle may stimulate skin by using a needle of a small size, or may form a small hole in skin to supply nutrients necessary for forming collagen to the dermal matrix, thereby making it easy to penetrate chemicals. Accordingly, the micro needle may easily transfer chemicals of a high molecular weight, such as insulin or hormone materials through skin, may naturally treat burns or scars by penetrating the needle into the dermal matrix, and may achieve improvement of skin tones and aging by inducing generation of collagen.

Meanwhile, the types of micro needles may include a roller type in which a plurality of needles are implanted in a roller to be rotated and a stamp type in which a plurality of needles are implanted in a circular or angular plate to be vibrated forwards and rearwards. An example of the roller type micro needle is disclosed in Korean Utility Model No. 20-0428918.

Moreover, a micro needle driving device that automatically reciprocally moves the micro needle forwards and rearwards has been developed instead of the above-described roller type or stamp type, and such a micro needle driving device includes an inclined plate type that has an eccentric structure or a spring structure including a driving motor and a link eccentrically connected to the driving motor.

However, the eccentric type micro needle driving device has a relatively large number of components, deteriorates precision due to tolerances between the components, and generates much noise because it uses a large number of links to convert rotations of the driving motor into reciprocations. Further, the inclined plate type micro needle driving device having a spring structure deteriorates the functions thereof while significantly deteriorating the durability and restoring force of the spring due to its characteristics by which the inclined plate repeatedly reciprocates at a high speed.

DISCLOSURE

Technical Problem

The present invention provides a micro needle driving device that may be economical, may improve spatial utility, and may be precisely controlled due to a simple structure and a large number of components by suggesting a new structure, may be stably operated by linearly moving a micro needle part on the same axis as that of a rotary shaft, and may lower noise and improve durability at the same time.

Technical Solution

In accordance with an aspect of the present invention, there is provided a micro needle driving device in which a micro needle part is mounted at a tip end thereof such that the micro needle part is reciprocally moved, the micro needle driving device including a body having an accommodation space in the interior thereof, a driving motor that is provided in the accommodation space, a rotating unit that is shaft-coupled to a rotary shaft of the driving motor to be rotated and has a guide boss on an outer peripheral surface thereof, and a moving cam unit to which the micro needle part is coupled on one side thereof and in which the rotating unit is accommodated, which has a guide which has a shape that is curved along a lengthwise direction thereof and to which the guide boss is slidably connected, on an inner peripheral surface thereof to reciprocally linear move along as the rotating unit rotates.

Here, it is preferable that the moving cam unit includes a first moving cam into which the rotating unit is rotatably inserted on one side thereof and a front side of which is opened, and which has a first guide step that protrudes from an inner peripheral surface thereof to correspond to the closed curve of the guide, and a second moving cam which is coupled to a front side of the first moving cam, in which the micro needle part is coupled to a front side thereof and a rear side thereof is connected to the first moving cam, and which has a protruding second guide step that corresponds to the first guide step such that the guide is formed on an inner peripheral surface thereof.

Then, it is preferable that the first moving cam and the second moving cam are coupled to a coupling pin that passes through the first moving cam and the second moving cam.

Further, it is preferable that the guide may be a guide groove that is formed on an inner peripheral surface of the moving cam unit to draw a closed curve so as to be inclined along a lengthwise direction thereof, and it is also preferable that the guide may be formed on an inner peripheral surface of the moving cam unit to form a closed curve that allows an endless motion.

Further, it is preferable that a sliding groove is formed on a front side of the rotating unit and the second moving cam has a guide pin that is slidably inserted into the sliding groove.

Advantageous Effects

The micro needle driving device according to the present invention has the following effects.

First, because it does not require a complex structure such as a link for converting rotations of a driving motor into linear reciprocations, it is economical and has an excellent spatial utility due to a simple structure and a large number of components.

Second, because it does not generate an error control due to tolerances between components, a precise control is possible and RPMs can be easily controlled.

Third, because noise can be lowered and lowering of durability such as wear can be prevented, the whole durability of the product can be improved.

Fourth, because a micro needle part is linearly moved on the same axis as that of the rotary shaft of the driving motor, a stable operation is possible.

DESCRIPTION OF MAIN PARTS OF DRAWINGS

Figure 1:
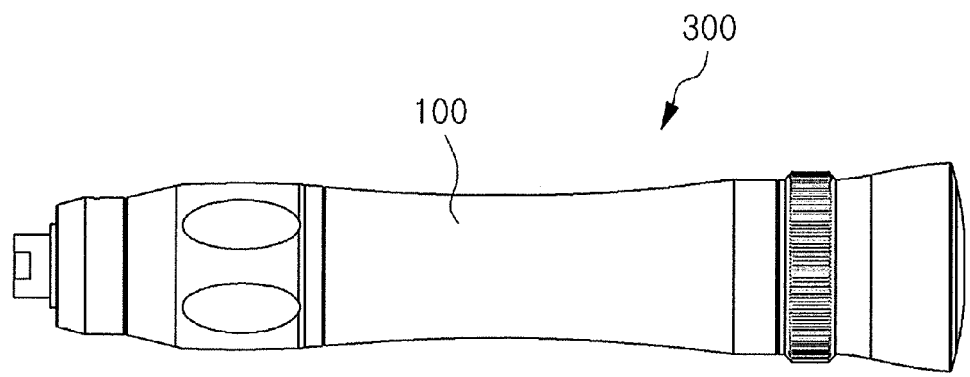
FIG. 1 is a front view illustrating an external appearance of a micro needle driving device according to an embodiment of the present invention.

100: Body
101: Accommodation space
210: Driving motor
212: Rotary shaft
220, 220*a*: Rotating unit
2202: Sliding groove
222: Guide boss
230, 230*a*: Moving cam unit
231: First moving cam
232, 232*s*: Second moving cam
2321: Mounting part
2322: Guide pin
233: Guide
2331: First guide step
2332: Second guide step
234: Coupling pin
300: Micro needle driving device

BEST MODE

Hereinafter, exemplary embodiments of the present invention will be described in detail with reference to the accompanying drawings.

Figure 2:
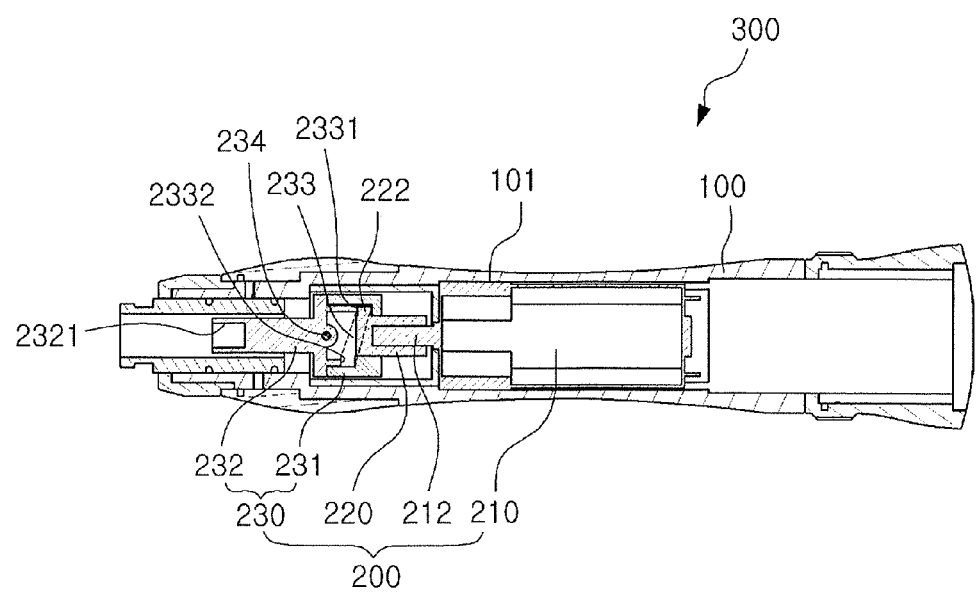
FIGS. 2 and 3 are sectional views illustrating an internal structure of the micro needle driving device of FIG. 1.
Figure 3:
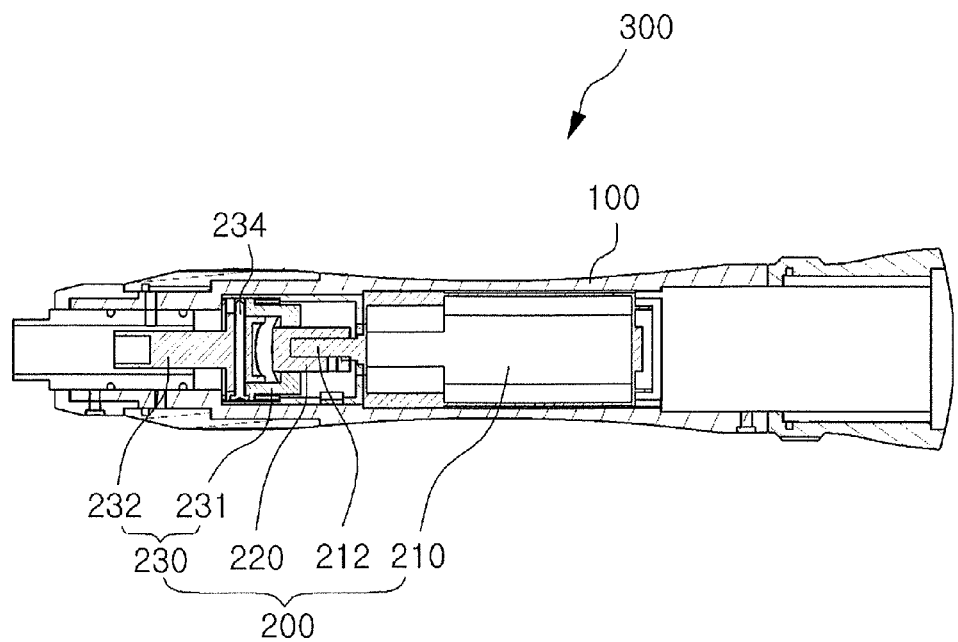

First, referring to FIGS. 1 to 3, a micro needle driving device 300 according to an embodiment of the present invention is adapted to automatically reciprocally move a micro needle part (not illustrated) that is mounted at a tip end thereof forwards and rearwards, and includes a body 100, a driving motor 210, a rotating unit 220, and a moving cam unit 230. Here, the micro needle part is a micro needle unit that includes one or a plurality of known micro needles, and a detailed description thereof will be omitted.

The body 100 has a substantially cylindrical rod shape that may be easily gripped by the user such that the micro needle part is slidably coupled to a front side thereof and an accommodation space 101 is formed in the interior thereof. Here, the body 100 may include a plurality of bodies that are assembled with each other as illustrated according the design thereof, and the structure and shape thereof may be modified into various forms.

Figure 4:
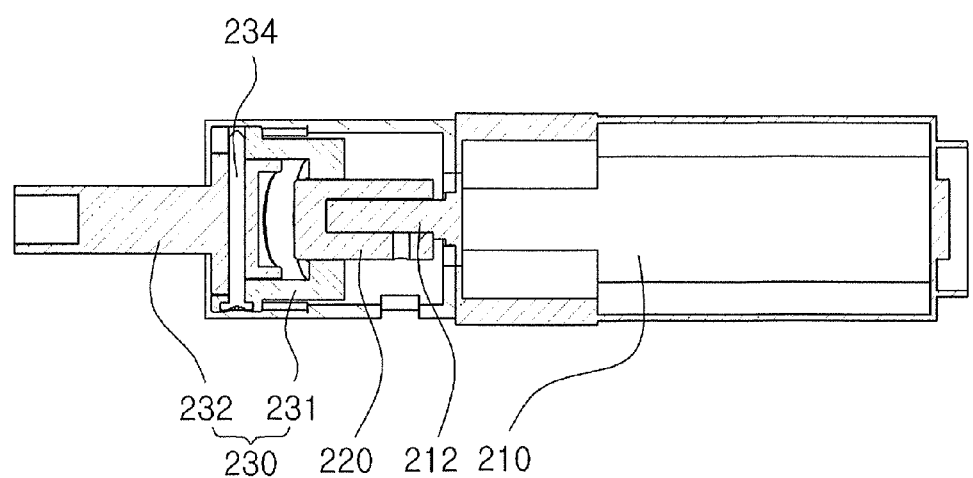
FIGS. 4 and 5 are sectional views illustrating a rotating unit and a moving cam unit of FIG. 2.
Figure 5:
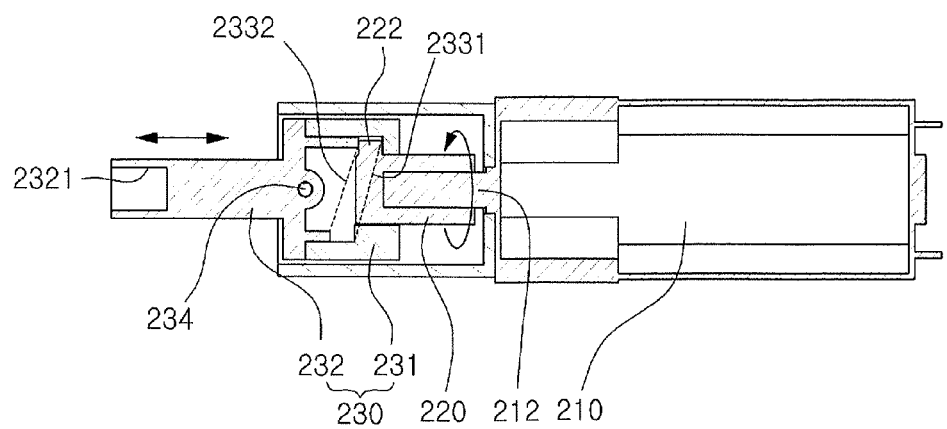

Referring to FIGS. 4 and 5, the driving motor 210 is provided in the accommodation space 101 of the body 100 to generate a rotational force. The driving motor 210 may employ various known motors, and a detailed description thereof will be omitted.

Meanwhile, although not illustrated, the micro needle driving device 300 may include a control unit that receives a signal from the user and controls an RPM and an on/off state of the driving motor 210. Further, the micro needle driving device 300 may be provided in the body 100 to be manipulated by the user, and may include a switch unit that sends a signal to the control unit such that an operation of the driving motor 210 is controlled through selection of the user.

Moreover, various embodiments may be applied to the driving motor 210, and for example, the driving motor 210 may receive electric power from the outside from a power battery or a power supply cable provided in the accommodation space 101 of the body 100.

The rotating unit 220 is shaft-coupled to a rotary shaft 212 of the driving motor 210 to be rotated, and has a cylindrical shape having a guide boss 222 on an outer peripheral surface thereof.

Although it is preferable that, as illustrated, the guide boss 222 be one boss that protrudes in a direction that is perpendicular to the rotary shaft 212 of the rotating unit 220 and protrudes from an outer peripheral surface of the rotating unit 220, various embodiments may be applied to the shape and the number of the guide bosses as long as the guide bosses may be moved along a guide 233, which will be described in an exemplary embodiment, to transmit a rotational force of the rotating unit 220 to the moving cam unit 230.

The moving cam unit 230 is slidably accommodated in the accommodation space 101 such that the micro needle part is coupled to one side thereof through a mounting part 2321 and the rotating unit 220 is connected to and accommodated on the inner side thereof, so that a rotational force of the rotating unit 220 is converted into a linear motion and the linear motional force is transmitted to the micro needle part.

In detail, a guide 233 to which the guide boss 222 is slidably connected such that the movement of the guide boss 222 is guided by the guide 233 is formed on an inner peripheral surface of the moving cam unit 230.

Here, the guide 233 is inclined along a lengthwise direction thereof and has a closed curve shape, such as a Moebius band, which is as if it performed an endless motion such that the guide boss 222 is rotated as the rotating unit 220 rotates and the moving cam unit 230 linearly moves in correspondence to the location of the guide boss 222.

Meanwhile, it is preferable that the guide 233 has a form of a guide groove in which the guide boss 222 is inserted and guided such the movement of the guide boss 222 is guided. However, this structure is simply an exemplary embodiment, and it is apparent that various embodiments may be applied in correspondence to the shape and structure of the guide boss 222 and a guide hole, through which the guide boss 22 is inserted, instead of the form of the above-described guide groove may be applied.

Further, the closed curve shape of the guide 233 may be variously determined according to a design, for example, of a linear motion distance of the moving cam unit 230, and the guide 233 may have various forms as long as the purpose thereof can be accomplished.

With regard to the moving cam unit 230, the moving cam unit 230 may have a plurality of configurations that are assembled with each other, instead of a single configuration, in consideration of a coupling aspect with the rotating unit 220 and a manufacturing method thereof.

In detail, the moving cam unit 230 includes a first moving cam 231 and a second moving cam 232 that are assembled with each other. The rotating unit 220 is rotatably inserted into and coupled to the first moving cam 231 on a rear side of the first moving cam 231 and a front side of the moving cam 231 is opened.

Further, a first guide step 2331 having a first guide surface that is inclined to correspond to the closed curve of the guide 233 protrudes from an inner peripheral surface of the first moving cam 231.

The second moving cam 232 is coupled to a front side of the first moving cam 231, the micro needle part is mounted on the second moving cam 232 through the mounting part 2321 formed on the front side the second moving cam 232, and a rear side of the second moving cam 232 is inserted into and coupled to the first moving cam 231. Further, a second guide step 2332 protrudes from an inner peripheral surface of the second moving cam 232 such that the guide 233 is formed to correspond to the first guide surface.

Here, the first guide step 2331 and the second guide step 2332 are formed such that the first guide surface and the second guide surface are spaced apart from each other at an interval to face each other such that the guide groove is formed by assembling the first moving cam 231 and the second moving cam 232.

Meanwhile, although it is illustrated in the embodiment that the guide 233 is formed through the first guide step 2331 and the second guide step 2332 in the structure in which the first moving cam 231 and the second moving cam 232 of the moving cam unit 230 are coupled to each other, this structure is simply an exemplary embodiment and various embodiments, such as a structure in which the guide 233 is formed only on an inner peripheral surface of the first moving cam 231, may be applied as long as the purpose thereof may be accomplished.

Moreover, although the first moving cam 231 and the second moving cam 232 are interference-fitted with each other to be assembled, the first moving cam 231 and the second moving cam 232 may be coupled to each other by a coupling pin 234 that passes through the first moving cam 231 and the second moving cam 232 as illustrated.

Figure 6:
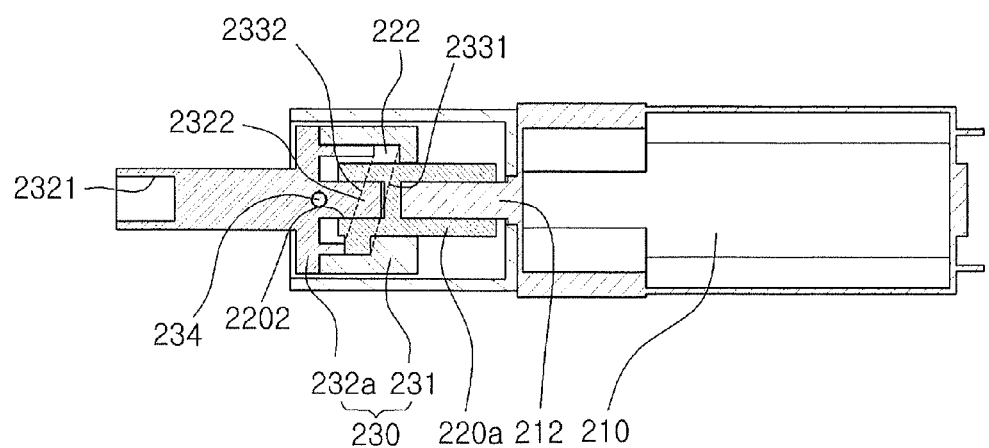
FIG. 6 is a sectional view illustrating another embodiment of the rotating unit and the moving cam unit of FIG. 5.

FIG. 6 is a sectional view illustrating another embodiment of the rotating unit 220a and the moving cam unit 230a. Referring to FIG. 6, the rotating unit 220a has a sliding groove 2202 on a front side thereof, and thus the second moving cam 232a has a guide pin 2322 that is slidably inserted into the sliding groove 2202. In this case, the second moving cam 232a allows the guide pin 2322 to be linearly moved more stably while being guided in the sliding groove 2202 during a linear movement thereof.

Meanwhile, in the micro needle driving device 300, because a rotary shaft 212 of the driving motor 210 and a mounting part 2321, on which the micro needle part are mounted, are situated on the same axis, the micro needle part is linearly moved on the same axis as that of the rotary shaft 212 of the driving motor 210. Accordingly, because the micro needle unit may maximally reduce an influence of an unnecessary moment or force that may be generated in the process of converting a rotational force of the driving motor 210 into a linear motion to transmit the rotational force of the driving motor 210, a stable linear motion is possible.

As described above, because the micro needle driving device 300 has a simple structure, the number of components can be reduced, allowing an economical and precise control thereof and improving durability.

Although one embodiment has been described above with reference to the accompanying drawings, it should be understood that this embodiment is given by way of illustration only, and that various modifications, variations, and alterations can be made without departing from the spirit and scope of the present invention. Hence, the true technical scope of the present invention will be determined by the technical spirit of the claims.

The invention claimed is:

1. A micro needle driving device in which a micro needle part is mounted at a tip end thereof such that the micro needle part is reciprocally moved, the micro needle driving device comprising:
   a body having an accommodation space inside thereof;
   a driving motor that is disposed in the accommodation space;
   a rotating shaft that is shaft-coupled to a rotary shaft of the driving motor to be rotated and has a guide boss on an outer peripheral surface thereof; and
   a moving cam assembly to which the micro needle part is coupled and in which at least a part of the rotating shaft is accommodated,
   wherein the moving cam assembly has a guide having a shape that is curved along a lengthwise direction of the moving cam assembly and disposed on an inner peripheral surface of the moving cam assembly,
   wherein the guide boss is slidably connected to the guide,
   wherein the moving cam assembly reciprocally and linearly moves along an inner surface of the body as the rotating shaft rotates, and
   wherein the rotating shaft has a sliding groove disposed on a front side thereof and the moving cam assembly has a guide pin that is slidably inserted into the sliding groove.

2. The micro needle driving device of claim 1, wherein the guide is a guide groove that is formed on the inner peripheral surface of the moving cam assembly to draw a closed curve so as to be inclined along the lengthwise direction of the moving cam assembly.

3. The micro needle driving device of claim 1, wherein the moving cam assembly comprises:
   a first moving cam into which the rotating shaft is rotatably inserted and a front side of the first moving cam is opened, wherein the first moving cam has a first guide step that protrudes from an inner peripheral surface of the first moving cam to correspond to the curved shape of the guide; and
   a second moving cam which is coupled to the front side of the first moving cam, wherein the micro needle part is coupled to a front side of the second moving cam and a rear side of the second moving cam is connected to the first moving cam, and wherein the second moving cam has a second guide step that protrudes apart from the first guide step such that the guide is formed on the inner peripheral surface of the moving cam assembly.

4. The micro needle driving device of claim 3, wherein the first moving cam and the second moving cam are coupled by a coupling pin that passes through the first moving cam and the second moving cam.

* * * * *